US009291536B2

(12) United States Patent
Kochmann et al.

(10) Patent No.: US 9,291,536 B2
(45) Date of Patent: Mar. 22, 2016

(54) BROADBAND ELECTROMECHANICAL SPECTROSCOPY

(71) Applicant: California Institute of Technology, Pasadena, CA (US)

(72) Inventors: Dennis M. Kochmann, Pasadena, CA (US); Charles S. Wojnar, Pasadena, CA (US); Jean-Briac le Graverend, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 29 days.

(21) Appl. No.: 14/246,731

(22) Filed: Apr. 7, 2014

(65) Prior Publication Data

US 2014/0298918 A1 Oct. 9, 2014

Related U.S. Application Data

(60) Provisional application No. 61/809,149, filed on Apr. 5, 2013.

(51) Int. Cl.
| | |
|---|---|
| *G01L 1/24* | (2006.01) |
| *G01N 3/02* | (2006.01) |
| *G01N 3/06* | (2006.01) |
| *H01F 1/01* | (2006.01) |
| *G01N 3/00* | (2006.01) |

(52) U.S. Cl.
CPC .. *G01N 3/02* (2013.01); *G01N 3/00* (2013.01); *G01N 3/068* (2013.01); *H01F 1/01* (2013.01); *G01N 2203/005* (2013.01); *G01N 2203/0073* (2013.01); *G01N 2203/0094* (2013.01)

(58) Field of Classification Search
CPC .......... G01N 3/068; G01N 2203/0094; G01N 2203/005; G01N 2203/0073; G01N 3/00; H01F 1/01
USPC ..................... 73/800, 862.324, 760
See application file for complete search history.

(56) References Cited

U.S. PATENT DOCUMENTS

| | | | | |
|---|---|---|---|---|
| 4,836,031 A | * | 6/1989 | Jatho et al. ...................... 73/800 |
| 5,025,658 A | * | 6/1991 | Elings et al. .................... 73/105 |
| 6,317,216 B1 | * | 11/2001 | Maris ............................. 356/496 |
| 7,705,331 B1 | * | 4/2010 | Kirk et al. .................. 250/493.1 |
| 2004/0017191 A1 | * | 1/2004 | Stanley ........................ 324/229 |
| 2006/0096385 A1 | * | 5/2006 | Wenski .......................... 73/800 |
| 2011/0299066 A1 | * | 12/2011 | Kusukame et al. ............. 356/51 |

OTHER PUBLICATIONS

Jaglinski, T., et al., "Composite Materials with Viscoelastic Stiffness Greater Than Diamond", Science, Feb. 2, 2007, pp. 620-622, vol. 315.
Franke, I., et al., "Anomalous piezoelectric and elastic properties of a tetragonal PZT ceramic near morphotropic phase boundary", Journal of Physics D: Applied Physics, 2005, pp. 749-753, vol. 38.

(Continued)

*Primary Examiner* — Max Noori
(74) *Attorney, Agent, or Firm* — Gates & Cooper LLP

(57) ABSTRACT

An apparatus, method, and material wherein the material's viscoelastic and/or fatigue life may be altered by application of a secondary tuning electromagnetic field or a selected temperature, and the material's viscoelastic and/or fatigue properties are measured by a mechanical response of the material caused by applying a primary driving electromagnetic field.

22 Claims, 16 Drawing Sheets

(56) References Cited

OTHER PUBLICATIONS

Avrahami, Y., et al., "Improved Electromechanical Response in Rhombohedral BaTiO3", Journal of Electroceramics, 2004, pp. 463-469, vol. 13.

Yang, P., et al., "Field-enhanced piezoelectric deformation during the high temperature/low temperature rhombohedral (FErh/FErl) phase transformation for tin modified lead zirconate titanate ceramics", Journal of Applied Physics, Jun. 15, 2002, pp. 10028-10031, vol. 91, No. 12.

Lakes, R.S., "Viscoelastic measurement techniques", Review of Scientific Instruments, Apr. 2004, pp. 797-810, vol. 75, No. 4.

Sawyer, C.B., et al., "Rochelle Salt as a Dielectric", Physical Review, Feb. 1, 1930, pp. 269-273, vol. 35.

Lakes, R.S., Viscoelastic Solids, CRC Press (1999).

Wojnar, C.S., et al., "Broadband control of the viscoelasticity of ferroelectrics via domain switching", Applied Physics Letters, 2014, pp. 162912-1-162912-4, vol. 105.

Le Graverend, J.B., et al., "Broadband Electromechanical Spectroscopy: characterizing the dynamic mechanical response of viscoelastic materials under temperature and electric field control in a vacuum environment", J. Mater. Sci. 2015, pp. 3656-3685, vol. 50.

\* cited by examiner

BROADBAND ELECTROMECHANICAL SPECTROSCOPY

CROSS REFERENCE TO RELATED APPLICATIONS

This application claims the benefit under 35 U.S.C. Section 119(e) of commonly-assigned U.S. Provisional Patent Application Ser. No. 61/809,149 filed on Apr. 5, 2013, by Dennis M. Kochmann, Charles S. Wojnar, and Jean-Briac le Graverend, entitled "ELECTRIC BROADBAND VISCOELASTIC SPECTROSCOPY,", which application is incorporated by reference herein.

BACKGROUND OF THE INVENTION

1. Field of the Invention

This invention relates to an apparatus and method which is designed to characterize the electro-thermo-mechanically-coupled mechanical and physical properties (e.g., the viscoelastic and fatigue properties) of materials, including ferroelectric materials as well as composite materials containing ferroelectric inclusions and having electromagnetically-tunable mechanical performance.

2. Description of the Related Art (Note: This application references a number of different publications as indicated throughout the specification by one or more reference numbers within brackets, e.g., [x]. A list of these different publications ordered according to these reference numbers can be found below in the section entitled "References". Each of these publications is incorporated by reference herein.)

In the quest for novel materials with extreme and tunable physical properties, active composite materials containing phase-transforming inclusions have been developed in recent years whose overall viscoelastic performance and properties (such as the dynamic stiffness and damping capacity) can be tuned by thermally controlling the phase transition[1]. In particular, experiments on Sn—$BaTiO_3$ composites [1,2] have confirmed extreme increases in dynamic stiffness and damping by orders of magnitude due to a thermally-activated transformation of the $BaTiO_3$ phase. However, it has also become evident that the need for a highly sensitive temperature control makes those materials unattractive for most practical applications. In contrast, materials with electromagnetically-controllable mechanical properties (e.g., materials that change their stiffness and damping by the push of a button) could serve numerous scientific and technological applications. Understanding and ultimately technologically exploiting such electro-thermo-mechanically-coupled time-dependent properties of materials (e.g., of ferroelectric materials or of composites containing ferroelectric phases) requires currently-unavailable measurement capabilities. Existing techniques of Broadband Viscoelastic Spectroscopy (BVS) [3] or Dynamic Mechanical Analysis (DMA) are insufficient because they cannot independently apply electromagnetic and mechanical loads under careful temperature control over wide ranges of frequency. A new apparatus and method that provide qualitative and quantitative data to characterize the electro-thermo-mechanically-coupled properties of materials enables the discovery of new active composites with extreme properties, of new ways to actuate existing materials, and of new physical phenomena.

SUMMARY OF THE INVENTION

The present invention discloses an apparatus for measuring one or more electro-thermo-mechanical properties of a material, including the material's viscoelastic and fatigue properties.

Specifically, one or more embodiments of the present invention disclose an apparatus, method, and material wherein the material's viscoelastic (e.g., stiffness, damping) and/or fatigue life may be altered by application of one or more secondary tuning electromagnetic fields or a selected temperature, and the material's viscoelastic and/or fatigue properties are measured by a mechanical response of the material caused by applying a primary driving electromagnetic field. The secondary tuning electromagnetic field and/or temperature can induce a structural transition in the material.

The apparatus can comprise one or more electromagnetic coils for generating the primary driving electromagnetic field that produces the mechanical response of a specimen comprised of the material during application of the secondary tuning electromagnetic field or selected temperature; and a detector positioned to receive a laser beam reflected from a mirror attached to the specimen to detect a specimen motion, wherein the specimen's motion results from the mechanical response and is used to measure the viscoelastic and/or fatigue properties of the material during application of the secondary tuning electromagnetic field and the selected temperature.

A specimen grip for physically holding/gripping the specimen can be provided inside the apparatus, wherein the specimen grip electrically isolates the specimen from the apparatus and applies the secondary tuning electromagnetic fields.

A clamp for attaching a permanent magnet to the specimen can be provided, wherein the permanent magnet converts the applied primary electromagnetic field to a mechanical force on the specimen, the mechanical force causes the mechanical response of the material in the specimen, and the clamp is electrically isolated from the specimen.

A laser can be positioned to focus the laser beam on the mirror on the specimen, wherein motion of the laser beam is used to measure the mechanical response of the material during application of the electromagnetic fields and the selected temperature.

One or more embodiments of the invention allow multi-axial bending and torsional loads (and combinations thereof) to be applied to a material sample and measuring the resulting material response in a contactless way, while e.g. heating the sample via radiation to a selected temperature (without the need for heated airflow), while e.g. exposing the sample to a vacuum environment (in avoidance of spurious damping due to air motion), while e.g. applying selected voltages to the specimen surfaces (to generate well-controlled electromagnetic bias fields within the material). Mechanical loads, thermal and electric fields, and ambient pressure can be controlled independently; frequencies of mechanical and electrical drivers can be varied across decades of frequency. For example, in one or more embodiments, the apparatus can measure an electromechanical response corresponding to a strain of $10^{-3}$ or less, as a function of one or more mechanical frequencies in a range of 0.01 Hz to 1 MHz, and as a function of applied electric fields having a frequency range of 1 mHz to at least 10 Hz and a magnitude of up to 5 MV/m.

One or more embodiments of the invention encloses the apparatus in a massive chamber with vacuum seal and wall-internal cooling to allow for safe operation at high temperature using internal radiant heaters and under high electric fields and/or to remove environmental noise from measurement data.

One or more embodiments of the present invention necessitate and apply this new apparatus for electro-thermo-mechanically-coupled testing using Broadband Electromechanical Spectroscopy (BES). For example, one or more embodiments of the present invention provide capabilities for uncovering new and beneficial material properties (e.g., the rare find of high stiffness and high damping) by the application of controlled mechanical, electrical and thermal fields to ferroelectric materials and composites thereof. For example, the previously-unexplored tunability of stiffness and damping in ferroelectric ceramics over wide ranges of mechanical and electrical frequencies (leading to damping increases of more than 600% and stiffness variations by more than 60%) is disclosed based on experimental data achieved with the new apparatus. In addition, one or more embodiments of the invention facilitate the discovery of new compositions of matter obtained by fabrication and optimization using the new apparatus (such as composites containing ferroelectric materials). To this end, BES is applied to samples of bulk ferroelectrics, ceramics, and composites (e.g., fabricated by techniques of powder-metallurgy) to determine their viscoelastic properties and to identify optimal material combinations and composite arrangements.

BRIEF DESCRIPTION OF THE DRAWINGS

Referring now to the drawings in which like reference numbers represent corresponding parts throughout:

FIGS. 1(a)-(b) illustrate cross-sectional schematics of BES setups according to one or more embodiments of the invention, wherein FIG. 1(a) and FIG. 1(b) illustrate the single- and double-cantilever configurations in bending, respectively. FIG. 1(a) is a preferred embodiment of this invention, FIG. 1(b) illustrates a possible variation.

FIG. 2(a) is a drawing of a representative specimen gripped at its bottom end and with magnet and mirror attached at its top end using a clamp that is surrounded by Helmholtz coils to apply the (primary) driving electromagnetic field. FIG. 2(b) is a drawing of the apparatus with its optical setup comprising laser and position sensor to measure the sample's deformation. FIG. 2(c) is a drawing of the electrically isolated grip used to attach the specimen to the apparatus and to apply the (secondary) tuning electromagnetic field. FIG. 2(d) shows a side-view drawing of a representative specimen with the specialized clamp attaching a (permanent) magnet and mirror to the sample's free end. FIG. 2(e) is a front-view drawing of the same specimen with the mirror attached. FIG. 2(f) is a drawing of a representative heater element used inside the chamber enclosing the apparatus. FIG. 2(g) is a drawing of the support structure to carry the Helmholtz coils. FIGS. 2(h) and 2(i) are drawings of the vacuum pump attached to the specialized vacuum chamber to host the apparatus. FIG. 2(j) is a drawing of the pressure control unit demonstrating the achievable pressure of below $2*10^{-6}$ mbar. FIG. 2(k) is a drawing of example electronic equipment used to control the apparatus and to process its data.

DETAILED DESCRIPTION OF THE INVENTION

Figure 1A:
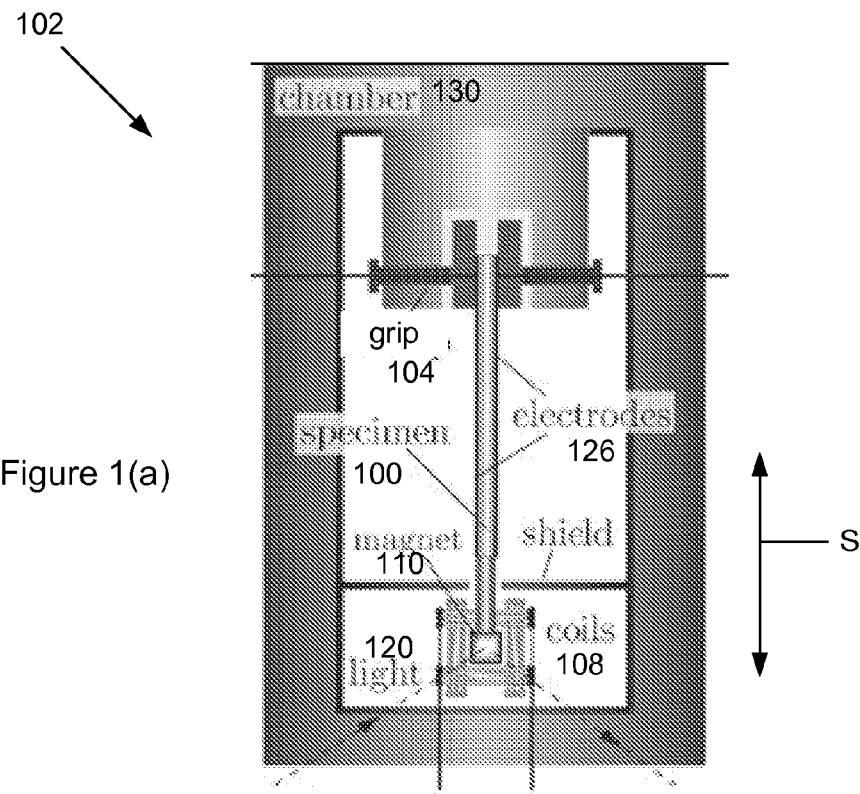

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

In one or more embodiments of the invention, the viscoelastic and fatigue properties of ferroelectrics and/or novel composite materials containing ferroelectric phases are measured. Ferroelectric materials and the ferroelectric phase in composites undergo a phase transition under certain combinations of mechanical stress, temperature, and electromagnetic fields. The phase transition can dramatically alter the measured physical properties of the material in the specimen (e.g. its viscoelastic and fatigue properties). Current methods that are used for measuring physical properties (e.g. the viscoelastic and fatigue response) of ferroelectrics and composites containing ferroelectrics can only apply mechanical stress and temperature; testing the fully electro-thermo-mechanical response of the materials of interest using current state-of-the-art methods (e.g. BVS) is not possible. Moreover, highly-accurate temperature control is not possible with current methods; BVS, for example, involves flowing heated air over the specimen, which can decrease the accuracy of the physical properties (e.g. viscoelastic and fatigue properties) that are measured. Methods and experimental equipment for investigating the response of ferroelectric and composites containing ferroelectric phases subjected to large ranges of electromagnetic fields while simultaneously applying large ranges of mechanical stress and temperature are unavailable. This lack of experimental methods and equipment has prevented the testing of ferroelectrics and novel composites containing ferroelectrics as tunable materials whose physical properties (e.g. viscoelastic and fatigue properties) can be dramatically altered by the push of a button—an entirely new design paradigm.

One or more embodiments of the present invention provide a novel experimental method and apparatus for performing broadband electromechanical spectroscopy to close this gap.

By being able to test such novel materials under varying electro-mechanical-thermal conditions, the materials become closer to being realized in technological applications; by gaining a better understanding of their response from experiments performed using this invention, the design of the envisioned novel materials can be improved.

For the envisioned composite materials to be tested, their viscoelastic moduli are on the order of $10$-$10^4$ GPa with damping measured by their loss tangent on the order of $10^{-6}$-1. Their large moduli require the material specimens in one or more embodiments of the present invention to be tested in bending and/or torsion as opposed to uniaxial tests typically used in current methods such as DMA, which are intended for materials with smaller viscoelastic moduli. In addition, one or more embodiments of the present invention utilize a contactless approach for applying mechanical forces to the specimens to avoid effects from the compliance of the apparatus, which is a problem in DMA when testing materials with stiff moduli. The large range of loss tangent requires, in one embodiment of the present invention, a high-precision laser-detector set up equipped with a lock-in amplifier. In addition, to achieve extremely accurate measurements of the viscoelastic moduli, the specimen, in one or more embodiments of the present invention can be placed inside a vacuum chamber with radiant heating to avoid artifacts of air damping on measurements of the specimen's physical properties. The overall size of the apparatus is determined by the specimen size to be tested, which itself is chosen so as to have a sufficiently high structural resonance frequency. In this way, the mechanical loading of the specimen in a particular embodiment of the invention can be chosen to be well below or near to the specimen's structural resonance frequency.

1. Apparatus

Based on the need to measure the electro-thermo-mechanical properties (e.g. viscoelastic and fatigue properties), the apparatus is designed in such a way to apply electromagnetic fields, mechanical forces, and temperature simultaneously. The fundamental set up of the apparatus is based on BVS [3] where specimens in one or more embodiments are tested in bending and/or torsion.

Figure 1B:
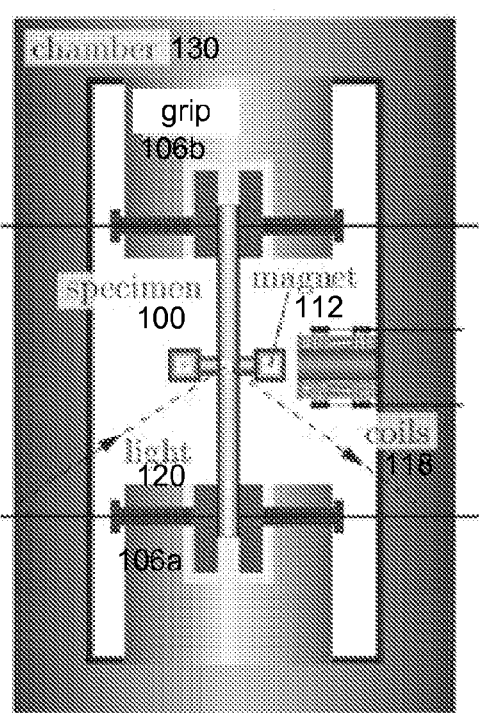
Figure 1C:
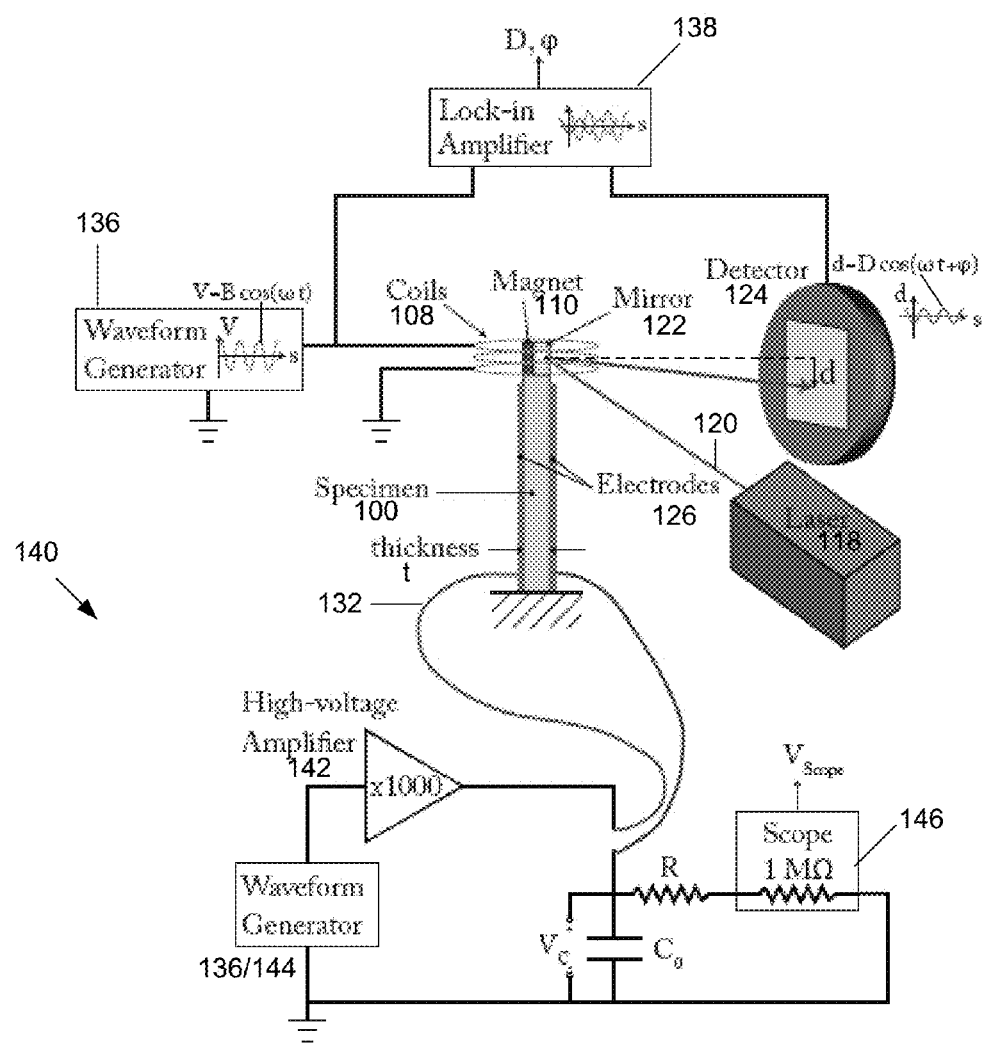
FIG. 1(c) schematically shows the complete setup of the apparatus connected to the electric circuit to apply the (secondary) tuning electromagnetic field to the specimen and to determine the polarization. The figure also illustrates the use of signal generators and processors (including e.g. laser and sensor, function generator, and amplifiers).
Figure 2A:
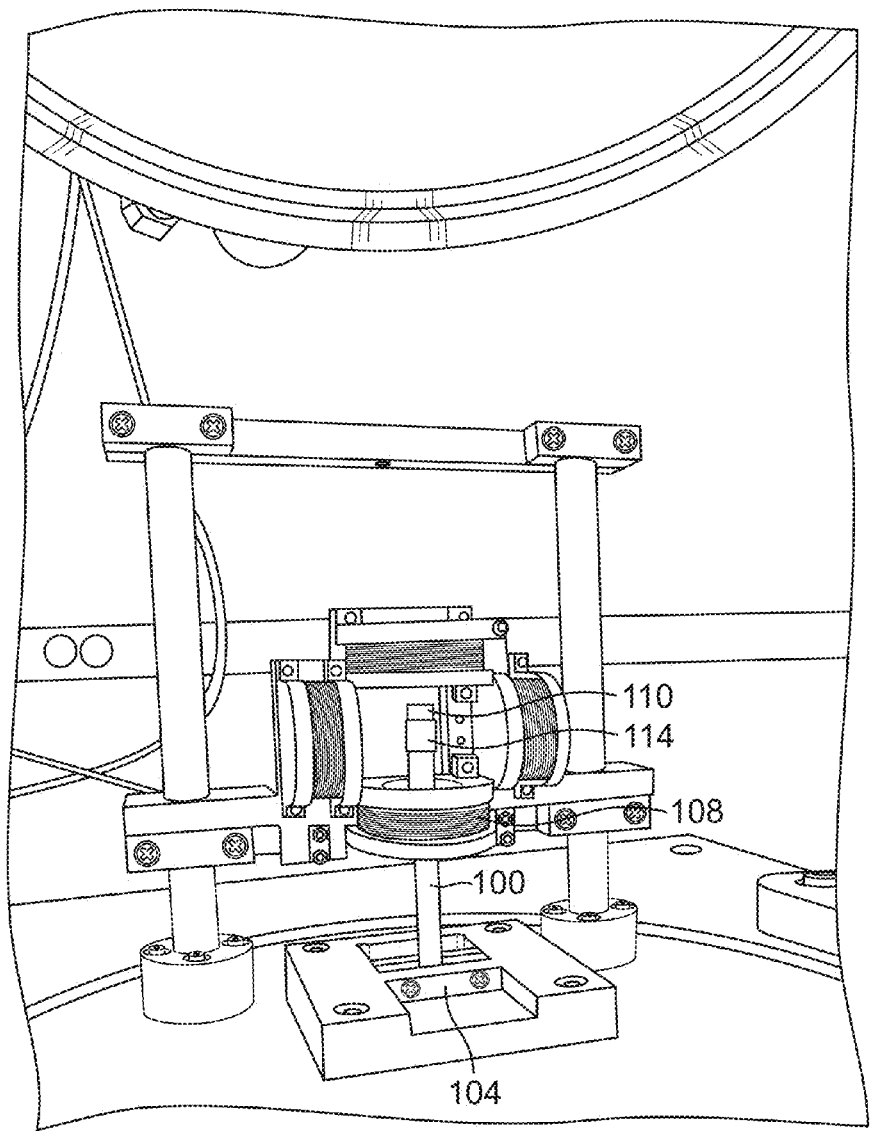
FIGS. 2(a)-(k) illustrate drawings of an apparatus according to one or more embodiments of the invention.
Figure 2B:
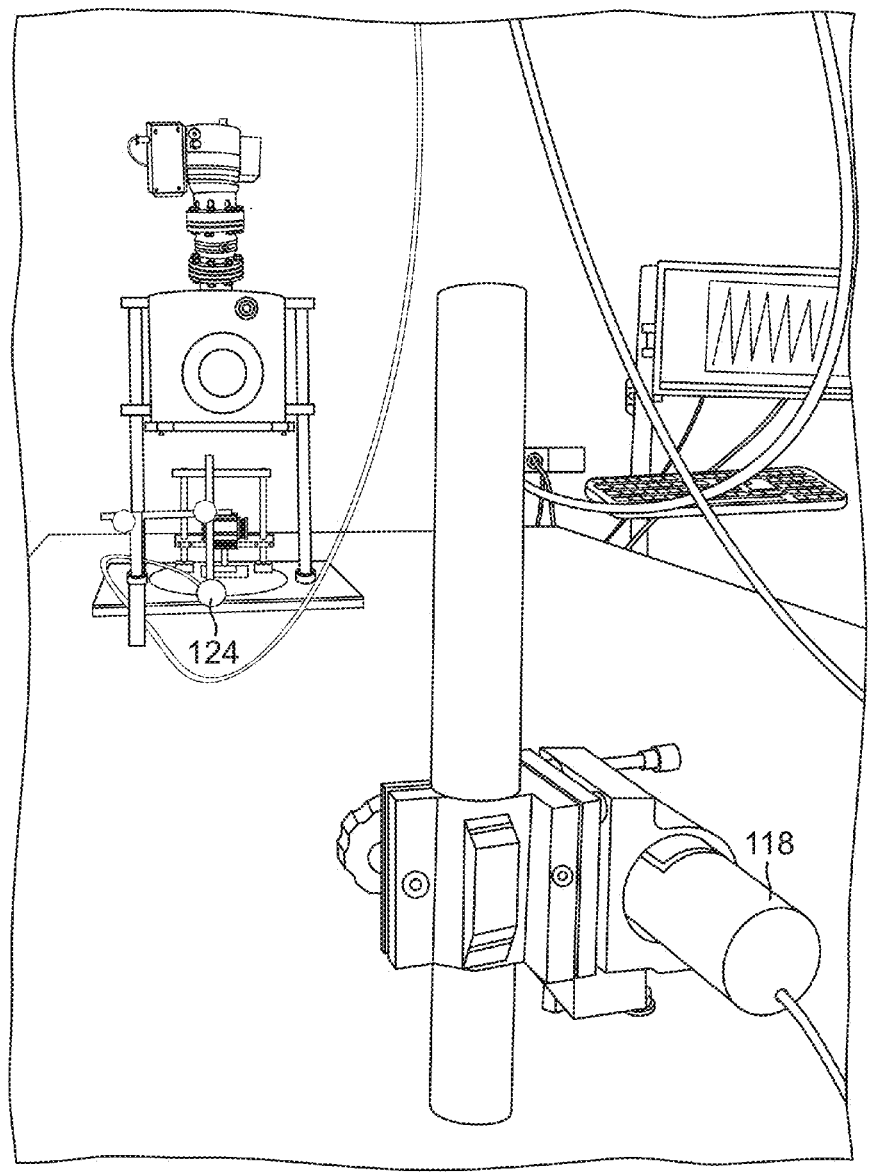
Figure 2C:
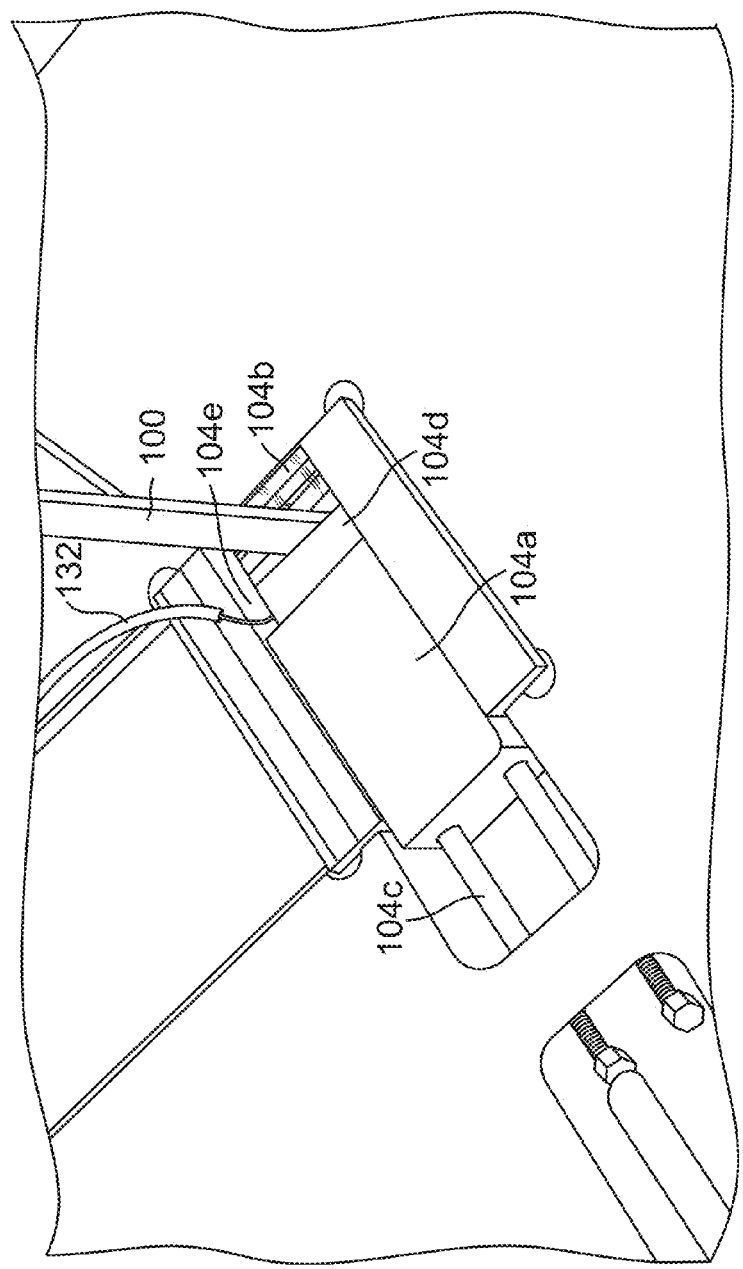
Figure 2D:
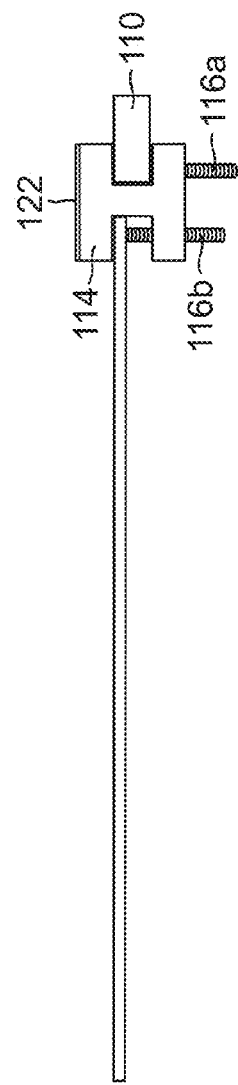
Figure 2E:
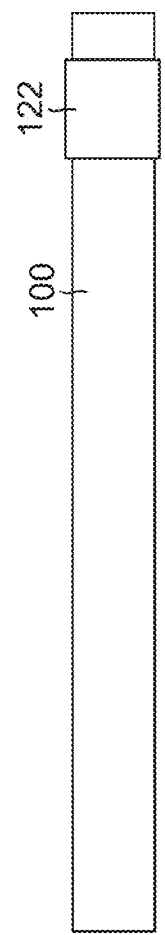
Figure 2F:
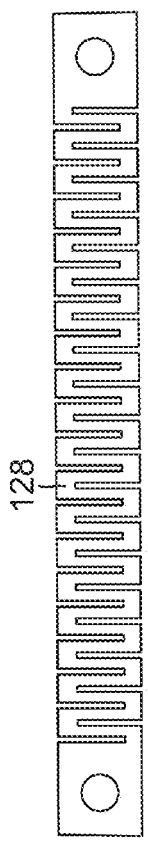
Figure 2G:
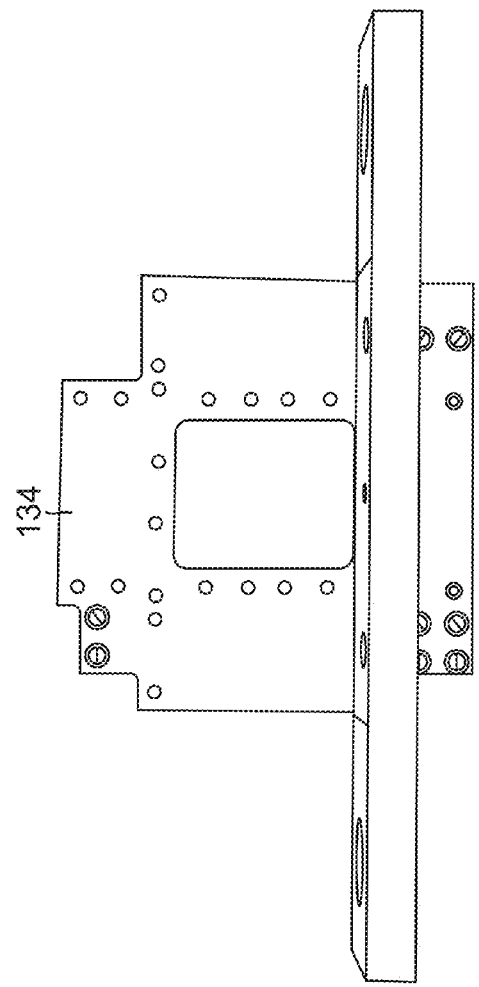
Figure 2H:
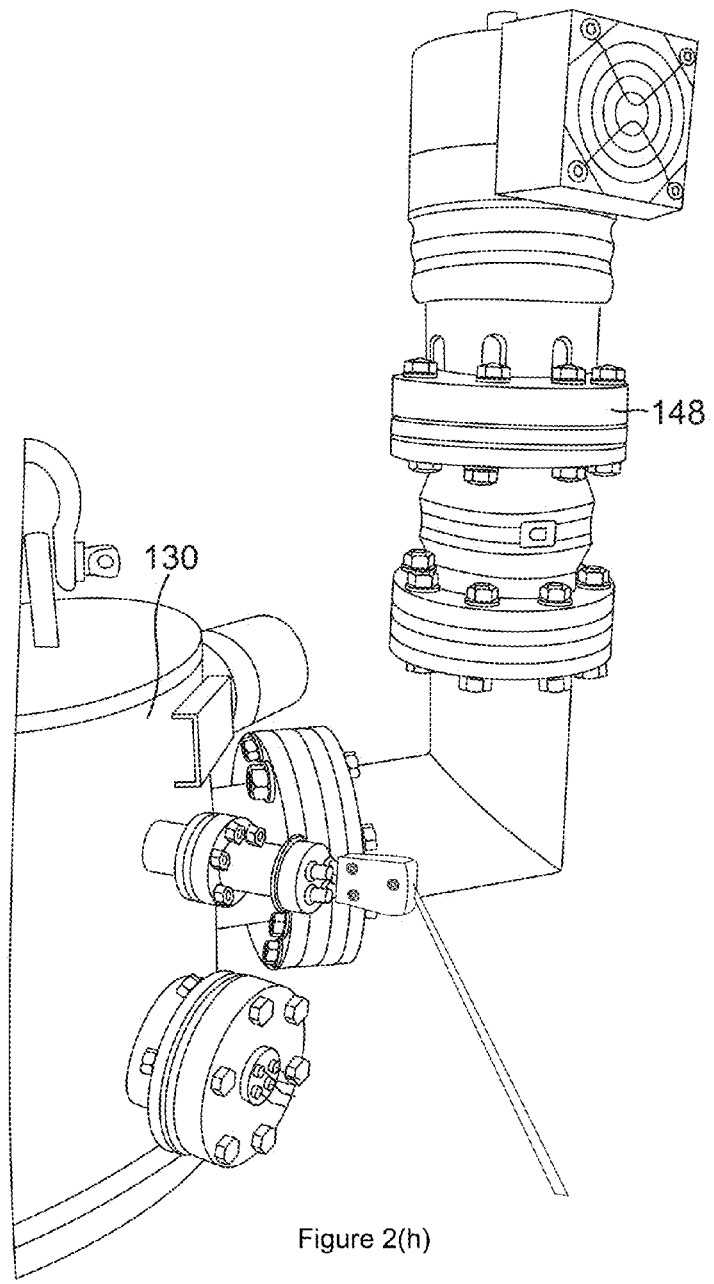
Figure 2I:
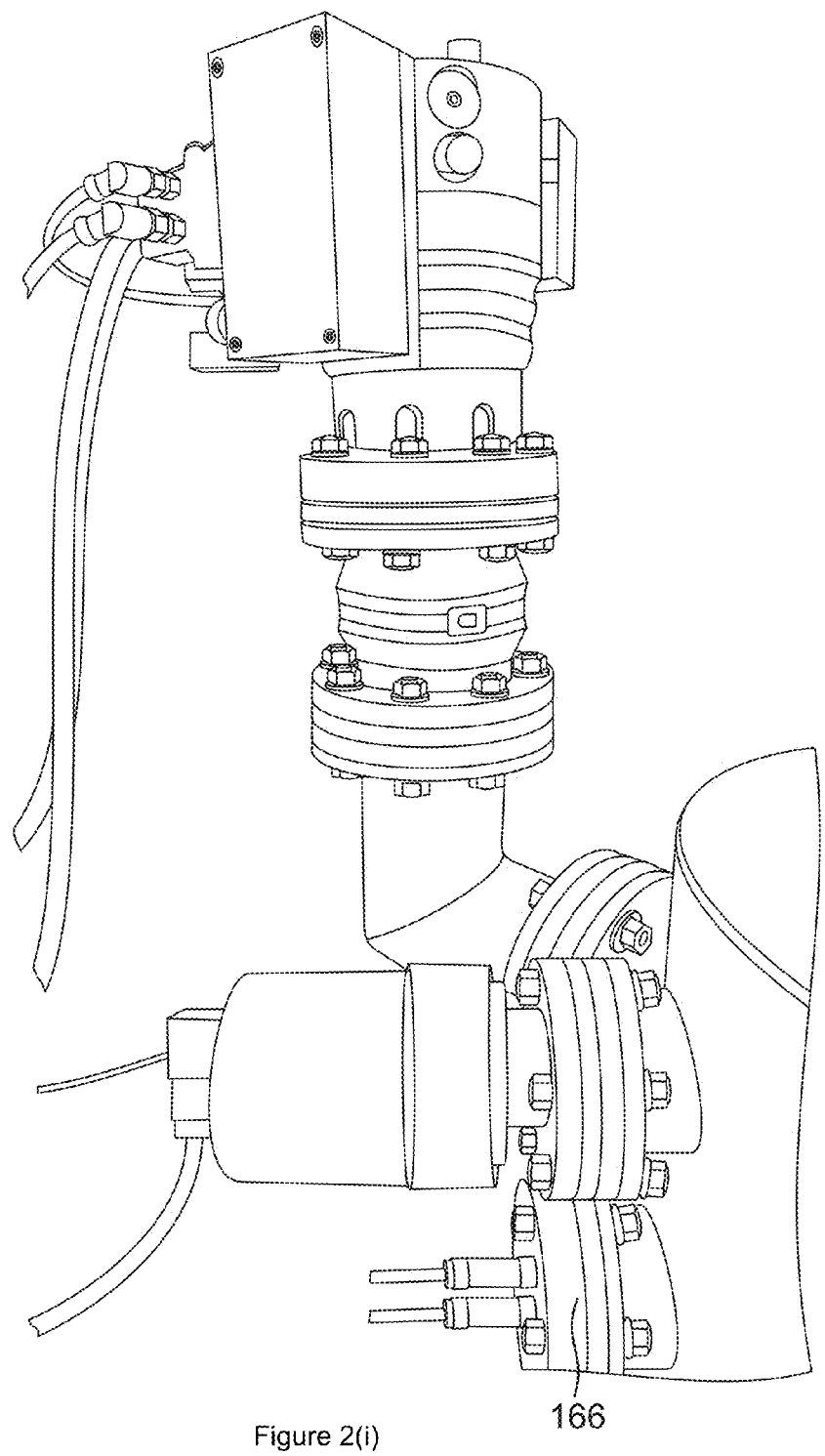
Figure 2J:
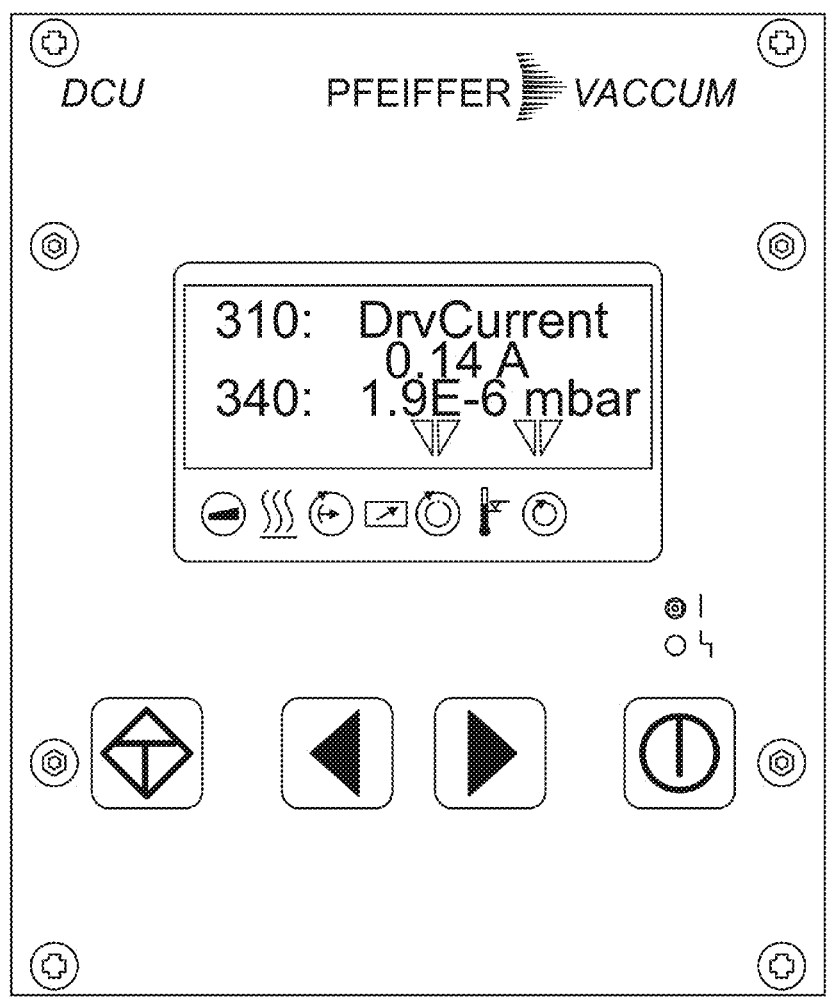
Figure 2K:
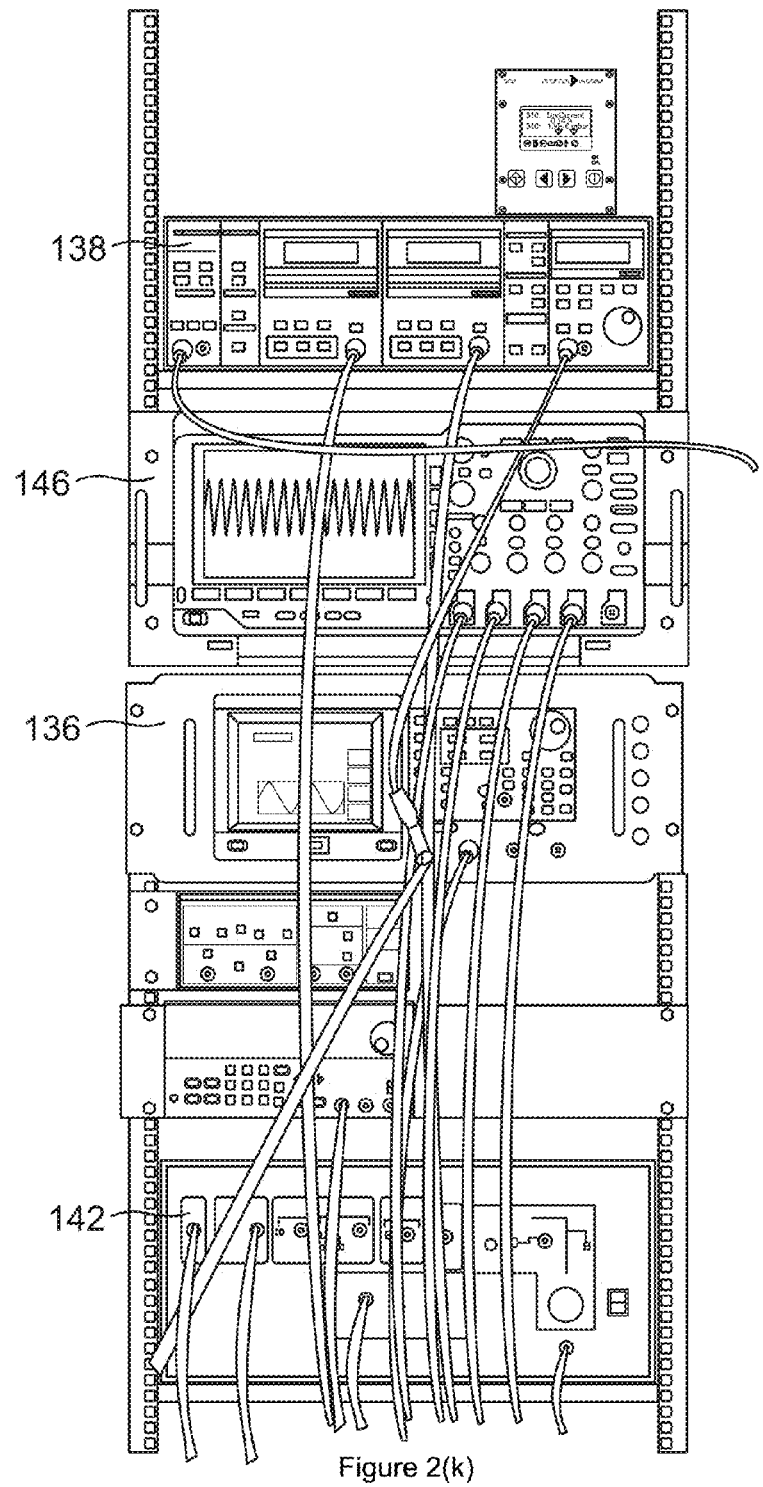

In one or more embodiments, the specimen 100 having thickness t and containing a material is held inside of the apparatus 102 via a grip(s) 104 or 106a and 106b for performing tests using a cantilevered beam or 3-point-bending geometry, respectively, as shown in FIG. 1(a-b). The physical properties (e.g. viscoelastic and fatigue properties) of the specimen are determined by the response of the material in the specimen due to mechanical forces induced by the driving electric field produced by Helmholtz coils 108 surrounding a magnet 110 or 112 attached to the specimen 100 as shown in FIGS. 1(a-b) and 2(a). In one or more embodiments, the driving electromagnetic field produced by the Helmholtz coils 108 applies a twisting and/or bending force to the magnet 110, which is attached to a clamp 114. The clamp 114 transfers the force on the magnet 110 to the specimen 100 via set screws 116a-b as shown in FIGS. 2(e-d). In one embodiment, the mechanical response of the specimen 100 is measured by a laser 118, which reflects a ray of light 120 off of a mirror 122 attached to the free end of the specimen 100 as shown in FIG. 2(b). The mirror 122 is attached to a clamp 114, which is itself attached to the specimen 100 via set screws 116a-b as shown in FIG. 2(e). The mechanical response of the material is captured by the movement of the ray of light 120 reflected from the mirror 122 in a detector 124. In one embodiment, the electro-thermo-mechanical behavior of the specimen 100 is observed by applying a tuning electromagnetic field to the specimen via surface electrodes 126 shown in FIG. 1(a-b) as well as controlling temperature via radiant heaters 128 as shown in FIG. 2(f) inside the vacuum chamber 130 during application of the driving electromagnetic field.

In a particular embodiment of the invention, the grips 104 or 106a-b hold the specimen 100 fixed inside the apparatus during testing. The grips 104 comprise sides 104a-b. One side 104a of the grips 104 is moveable by set screws 104c to tightly grip the specimen 100 as shown in FIGS. 2(a) and 2(c). In between the grips 104a-b and the specimen 100 are placed a stiff electrically insulating material (e.g. glass) 104d to prevent a short circuit between the specimen's surface electrodes 126 and the grips 104 or 106a-b. In addition the surface 104e of the insulating material 104d in contact with the specimen 100 is coated with a conducting material (e.g. copper tape) which is connected to the high-voltage source via wire leads 132. In this way, the tuning electromagnetic field can be applied to the specimen's surface electrodes 126 without the need to directly attach wire leads to the specimen 100, which may affect the measured mechanical response of the specimen.

One or more Helmholtz coils 108 are placed around the free end of the specimen 100 to generate the driving electric field. In a particular embodiment, the Helmholtz coils 108 are constructed by coiling wire around electrically insulating and non-magnetic cores (e.g. Macor). One embodiment of the apparatus has two pairs of coils as shown in FIG. 2(a) which can be used to apply a twisting and/or bending moment to the specimen. The Helmholtz coils are rigidly held in place by a supporting structure 134 shown in FIGS. 2(a) and 2(g). In one embodiment, current is passed through the coiled wire using a waveform generator 136 (e.g. Dual Channel Arbitrary Function Generator, Model: AFG 3022B, Tektronix, Inc. Beaverton, Oreg., USA) to generate a uniform magnetic field in between the pairs of coils 108. To avoid interference between the driving electromagnetic field generated by the Helmholtz coils 108 and the tuning electromagnetic field generated by surface electrodes 126 on the specimen 102, there must be separation distance S between the two (see e.g. FIG. 1 or FIG. 2(a)).

In one embodiment of the invention, the driving electromagnetic field generated by the Helmholtz coils 108 applies a force to the permanent magnet 110 that is attached to the specimen 100 via a clamp 114, thereby transferring the force on the magnet 110 to the specimen 100; this type of contactless approach to applying a mechanical force to the specimen 100 is important for reducing the effects the compliance of the apparatus 102, which increases the accuracy of measurements of the specimen's physical properties and improves upon existing methods such as DMA. The permanent magnet 110 is held in on one end of the clamp 114 via set screws 116a while the opposite end of the clamp 114 attaches to the specimen 100 also via set screws 116b as shown in FIGS. 2(d-e). The clamp 114 is constructed from a rigid material to effectively transfer the force from the magnet 110 to the specimen 100. The clamp 114 material must also be non-conducting and non-magnetic so not to interfere with the driving and or tuning electromagnetic fields. For testing materials under high temperatures in one embodiment of the invention, the clamp 114 material must also be stable over large temperature ranges (e.g. Macor). Finally, a mirror 122 is attached to the clamp 114 to reflect the incoming ray of light from a laser 118 (e.g. 5 mW 633 nm Helium-Neon Laser Model: LHRR-0500 Research Electro-Optics, Boulder, Colo., USA) into a detector 124 (e.g. SpotOn Analog Optical Beam Position and Power Measurement System Analog Version, Model: SPOTANA-9L, Duma Optronics Ltd., Nesher, Israel), which moves due to the mechanical response of the specimen 100. In one embodiment of the invention, the physical properties of the material in the specimen (e.g. its viscoelastic and fatigue properties) are measured by inputting the signal from the laser detector into a lock-in amplifier 138 (e.g. DSP Lock-In Amplifier, Model: SR830 Stanford Research Systems, Sunnyvale, Calif., USA) using as a reference the signal (e.g. V=B cos($\omega$ t), where V is voltage, B is amplitude, $\omega$ is frequency and t is time), from the waveform generator 134 used to generate the driving electromagnetic field. The lock-in amplifier 138 measures the amplitude D of the signal (e.g, displacement d=D cos ($\omega$ t) from the laser detector 124, which is related to the specimens' dynamic stiffness, as well as the phase lag $\phi$ between the signal from the laser detector and the reference signal, which is related to the specimen's loss tangent. In this particular embodiment of the invention, the viscoelastic properties of the specimen are characterized by its dynamic stiffness and loss tangent according to standard procedures (e.g. described in [4]). In one particular embodiment, the tuning electromagnetic field is generated by applying a voltage across the specimen via surface electrodes 126 (e.g. nickel electrodes of negligible μm thickness applied via a sputtering technique). In one embodiment, the surface electrodes 126 are in contact with the conductive coating 104e on the insulating material 104d between the specimen 100 and the grip 104. The conductive coating 104e is attached to a high-voltage source via wire leads 132. Under large applied tuning electromagnetic fields, phase transformations may occur in ferroelectric and composites containing ferroelectrics that are tested using this apparatus. A Sawyer Tower circuit shown in FIG. 1(c) is used to be able to detect such phase transformations [5]. In a particular embodiment of the invention a 100 μF capacitor $C_0$ and 13 MegaOhm (MΩ) resistor R are used in the Sawyer Tower circuit (voltage across the capacitor is $V_c$). Detection of the phase transformations is important for fully characterizing the electro-thermo-mechanical response of the material in the specimen 100. Currently available methods such as BVS do not have such an electronic circuit for applying a tuning electromagnetic field to specimens. In one or more embodiments, the circuit 140 for applying the fields further includes a high voltage amplifier 142, a waveform generator 144, and an oscilloscope 146 with 1 MΩ resistance measuring Vscope. In one or more embodiments, waveform generator 144 can be the same as waveform generator 136 (i.e., waveform generator 136 can have two outputs that can be independently controlled to apply the primary driving and secondary tuning electromagnetic fields). In other embodiments, it is possible to use two separate waveform generators 136, 144.

In one embodiment, the apparatus can be enclosed in a vacuum chamber 130 to remove damping effects from the air and also to add the capability to accurately control temperature (up to 400° C.) by radiant heaters 128 placed inside of the chamber 130. In a particular embodiment of the invention, the vacuum is achieved by a Pfeiffer vacuum system 148 as shown in FIGS. 2(h-i). This method improves upon currently available BVS techniques by replacing the heating by convection approach using airflow over the specimen by a radiative heating approach, thereby enhancing the accuracy of measurements of the specimen's physical properties by reducing vibrations in the specimen caused by the airflow. Furthermore, the vacuum chamber also improves upon current BVS techniques by completely removing the damping effects caused by the surrounding air.

Experiments with this apparatus have yielded rich sets of otherwise unavailable electro-thermo-mechanical data on the behavior of ferroelectric materials, which is a necessity for tailoring their physical properties according to one goal of the present invention.

2. Broadband Electromechanical Characterization of Ferroelectric Ceramics

BES of samples made of pure ferroelectrics can be used to measure damping and stiffness changes during microstructural domain wall motion under varying electric fields. These measurements can be used to determine which ferroelectric materials exhibit significant dynamic moduli softening under electric fields, and which ferroelectric materials display the greatest potential to exhibit a temporary negative-stiffness effect during transformation when embedded in a composite.

Beneficial material properties arise from two physical effects. First, controlling the domain wall motion and repolarization process in ferroelectric materials by an applied bias electric field can lead to strong changes of the mechanical properties, specifically of the viscoelastic performance and properties (including stiffness and damping). One or more embodiments of the present invention enable the identification of optimal frequencies of the applied bias electric field (at least between 1 mHz and 10 Hz) and mechanical frequencies (between 0.01 Hz and 1 MHz) to produce strong variations of the mechanical properties. Second, embedding ferroelectric inclusions in a ceramic matrix constrains the structural rearrangements and can give rise to a negative-stiffness effect. The more pronounced the softening behavior of bulk ferroelectrics, the stronger the expected effect on the overall viscoelastic properties of composites. Therefore, one or more embodiments of the present invention can study the dynamic softening of ferroelectric ceramics under varying electric fields in order to identify ferroelectric materials of great potential for active composites. Barium titanate (in doped and undoped compositions) has already shown extreme stiffness and damping anomalies in a tin matrix under temperature control[1]; its ferroelectric character qualifies it as an ideal initial candidate for the proposed experiments; zirconium and lead titanate display similar behavior [6,7] and can also be studied. Doping of titanate compounds [8] has shown promising effects both on the transition and on the softening behavior. Therefore, experiments can involve undoped, and metal- and ceramic-doped samples.

Figure 3:
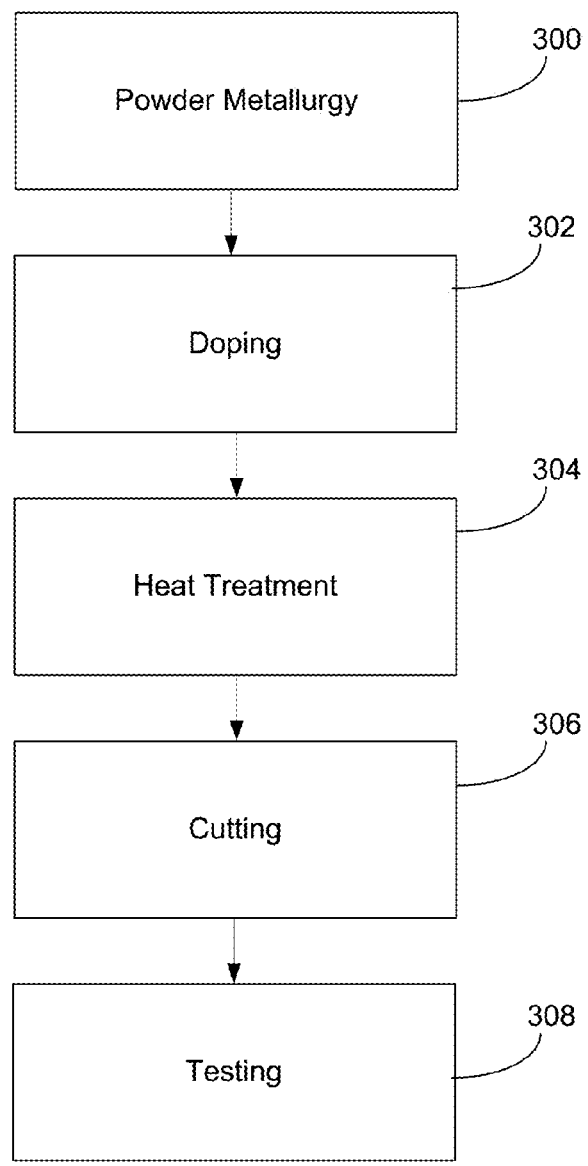
FIG. 3 illustrates a method of fabricating ceramic materials (e.g. bulk ferroelectric ceramics) at different frequencies of the (secondary) tuning electric field from 0.01 Hertz (Hz) to 1 Hz according to one or more embodiments.
Figure 4:
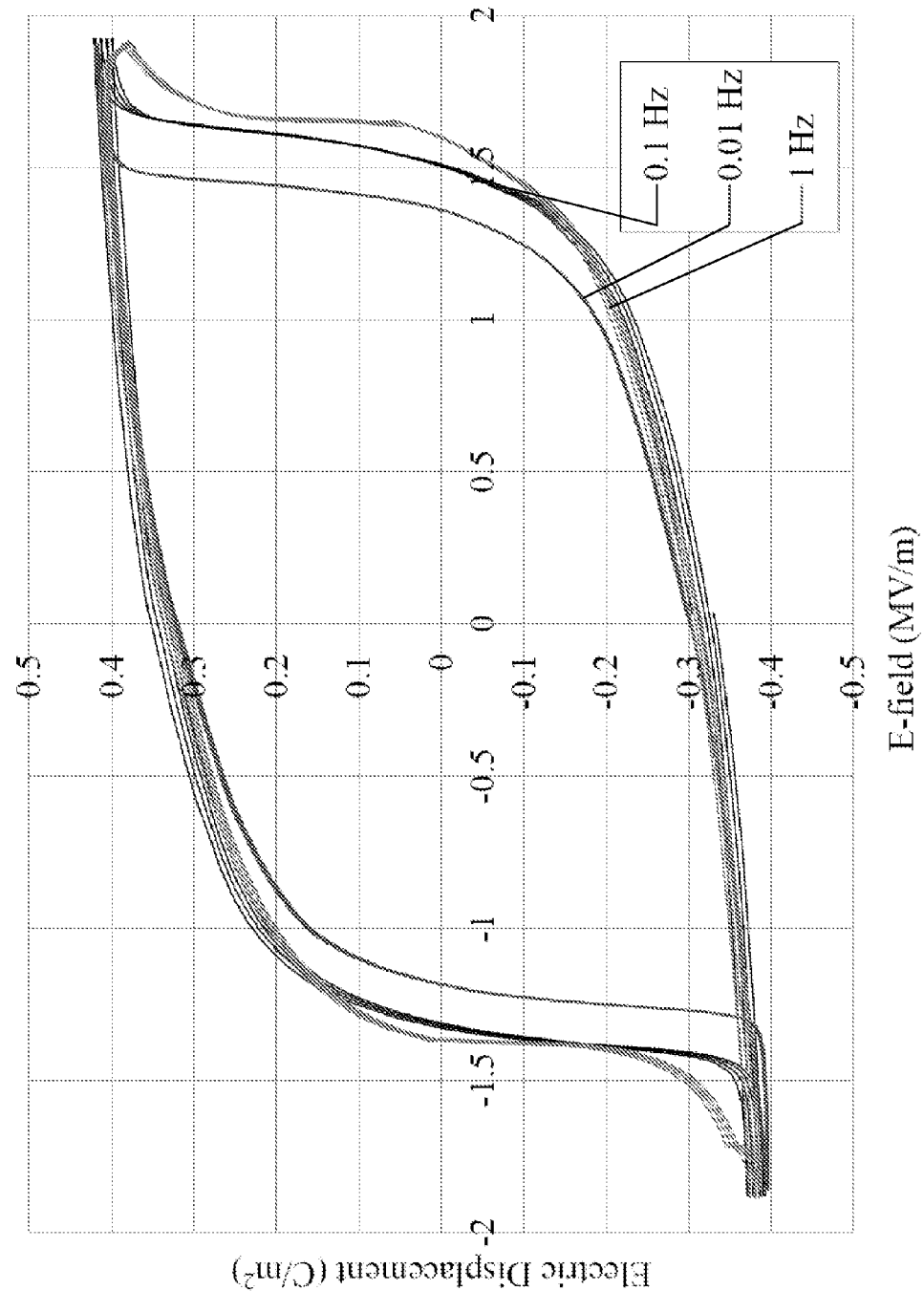
FIG. 4 plots polarization (P) in $C/m^2$ vs. applied (secondary) tuning electromagnetic field (E) in Megavolts per meter (MV/m) for bulk lead zirconate titanate (PZT), as measured using the apparatus of FIGS. 2(a)-(k) and according to one or more embodiments of the invention. In particular it shows the rate sensitivity of PZT to tuning electric field frequencies of 0.1 to 1 Hz, which is an important behavior to understand when fabricating future ferroelectric and ferroelectric specimens.

FIG. 3 illustrates a method of fabricating and testing a ferroelectric ceramic according to one or more embodiments. Specimens are fabricated by powder metallurgy (blending, compacting, sintering of pure fine-ground and sieved ceramic powders), as illustrated in Block 300, the addition of optional dopants is illustrated in Block 302, followed by heat treatment, as illustrated in Block 304. Samples are cut by a diamond saw and polished, as illustrated in Block 306.

Figure 6:
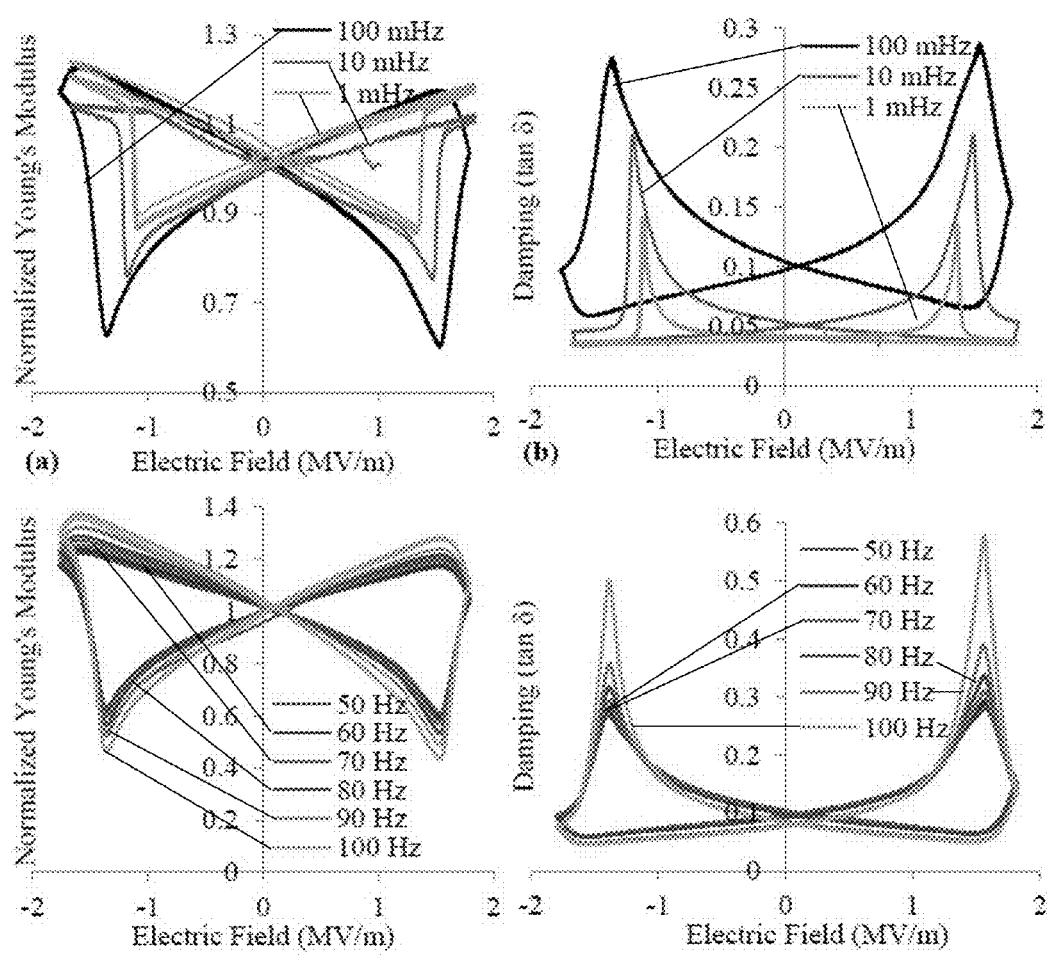
FIG. 6 plots variation of (a) dynamic stiffness and (b) damping versus applied (secondary) tuning electromagnetic field for different cycling frequencies of the applied tuning electromagnetic field of 1, 10, and 100 milliHertz (mHz) and fixed mechanical loading induced by the driving electromagnetic field at 50 Hz; variation of (c) stiffness and (d) damping versus applied tuning electromagnetic field for different mechanical bending frequencies induced by the driving electromagnetic field (50-100 Hz) and fixed tuning electromagnetic field cycling frequency of 100 mHz, as measured using the apparatus of FIGS. 2(a)-(k) for bulk PZT, and according to one or more embodiments of the invention.

Testing, as illustrated in Block 308, involves BES at variable frequencies in the subresonant regime (0.01 Hz-ca. 200 Hz) with and without applied tuning electromagnetic fields of variable voltage (up to 10 MV/m) in order to characterize the mechanical softening behavior during induced domain wall motion and to identify ferroelectric materials with pronounced viscoelastic softening and with strong damping increases. For example, FIG. 6 illustrates experimental data for lead zirconate titanate (PZT) obtained from one or more embodiments of the present invention, which demonstrate stiffness changes by more than 50% and damping increases by more than 500% under appropriately-controlled applied tuning electromagnetic fields.

One or more embodiments of the present invention can include a comprehensive experimental campaign to determine the viscoelastic properties of bulk ferroelectric ceramics, e.g., of barium titanate ($BaTiO_3$) and lead zirconate titanate (PZT), under varying electric fields. Results using BES have shown that well-controlled ferroelectric domain-switching under an applied tuning electromagnetic fields can be used to control the mechanical properties over wide ranges as well as to reach novel combinations of viscoelastic properties during this process (see FIG. 6). Findings confirm the expected mechanical instability (visible as a clear stiffness drop during domain switching at the critical electric field), which forms the basis of composite materials according to one or more embodiments of the invention.

3. Fabrication of Composites with Ferroelectric Inclusions in a Ceramic Matrix

Ceramic-based composites with ferroelectric inclusions can be fabricated using methods of powder metallurgy and heat treatment. The matrix material must satisfy two main purposes: to enforce a stiff geometric constraint on the particulate inclusions, and to function as an electric insulator between the electrodes attached to the sample's surfaces. When a sufficiently-high bias electric field is applied, the matrix prevents the inclusions from undergoing structural changes which results in a so-called negative-stiffness effect. Under an applied electric voltage near or above the coercive field, domain wall motion will be induced and the material's polarization is changed permanently. When constrained by a stiff matrix, such mechanisms are temporarily prevented and give rise to the negative-stiffness effect. In combination with a stiff matrix, such negative stiffness in the inclusion phase can give rise to strong overall stiffness and damping variations [1]. Composites can be fabricated and tested using BES to determine optimal candidates for the composite's stiff matrix phase and the active inclusion phase, and how to optimize volume fractions and particle distribution.

Figure 5:
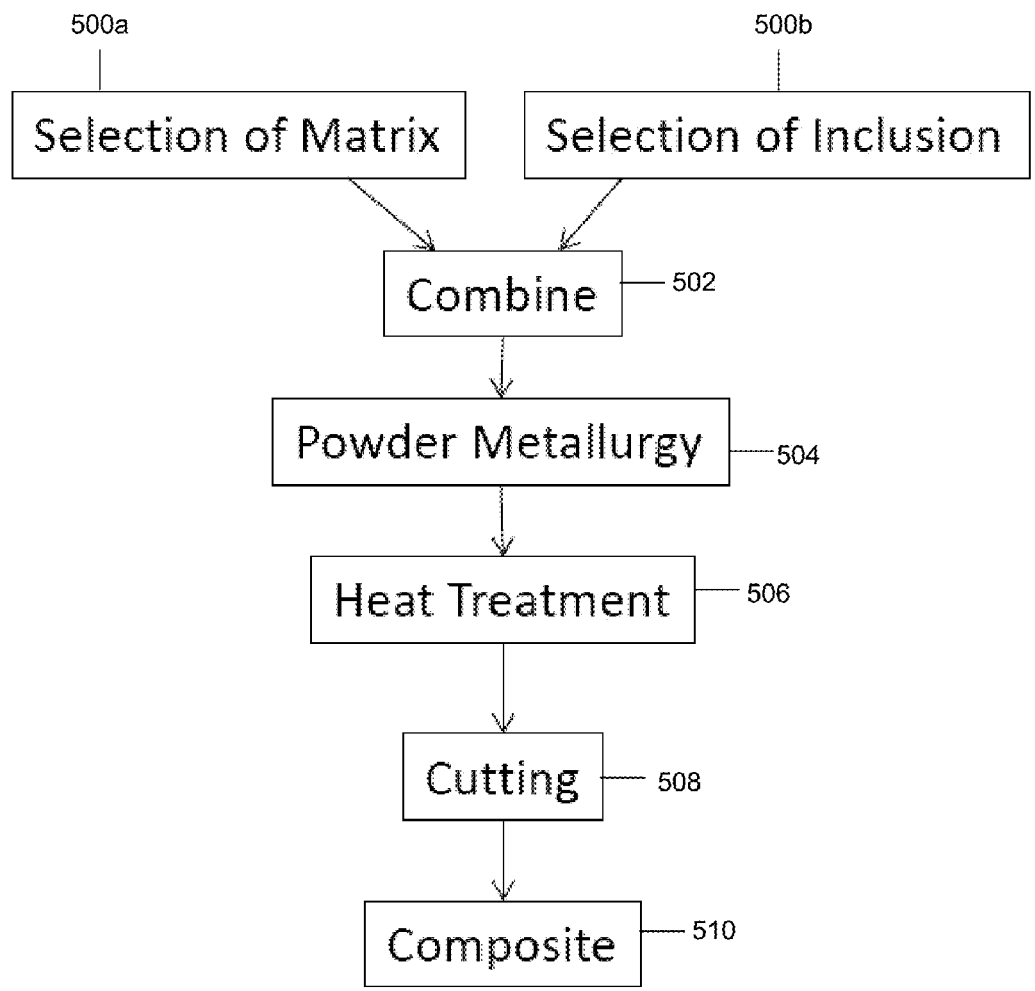
FIG. 5 illustrates a method of fabricating a composite according to one or more embodiments of the invention.

FIG. 5 illustrates a method of fabricating a composite, according to one or more embodiments. Matrix materials are selected and derived (Blocks 500a) from fine-ground powder. Various sizes of polycrystalline inclusion particles can be selected and derived (Block 500b) from the methods in section 2. Powders and particles are blended/combined (Block 502), compacted and sintered by methods of powder metallurgy (Block 504) followed by heat treatment (during which an external electric bias can be applied to introduce a polarization in the material) (Block 506), and cut using a diamond saw (Block 508) resulting in a composite (Block 510). For comparison, additional reference samples of the pure matrix materials are fabricated using the same technique.

4. Viscoelastic Properties of Electrically Tunable Ferroelectric Materials

Domain wall motion in ferroelectric and piezoelectric materials is well-known as a physical mechanism to accommodate changes of polarization and can be used to dissipate energy e.g. when embedded in a metal matrix [1] to achieve damping. Here, a new mechanism is exploited: induced domain wall motion by a bias electric field applied to the material. This mechanism allows fine-tuning of the domain reorientation process by a sophisticated control of the (secondary) tuning electromagnetic field.

One or more embodiments of this invention enable testing of the effective mechanical properties (e.g., the viscoelastic performance including stiffness and damping) at mechanical loading frequencies from 0.01 Hz to 1 MHz (applied by the primary driving electromagnetic field) while an electric field is applied at frequencies from 0.01 Hz to 1 MHz (applied by the secondary tuning electromagnetic field). For example, FIG. 6 illustrates strong increases in damping (by more than 500%) and large variations in stiffness (by more than 50%) obtained from PZT samples using one or more embodiments of this invention.

Through numerous experiments, we see the increase in damping and softening become more pronounced with increasing electric cycling frequency and for increasing mechanical load frequency (see FIG. 6) due to controlled domain wall motion. These results yield important guidelines for composite design: the microstructure (e.g. grain size and composition) can be modified to affect the domain wall structure in a favorable manner, and electric and mechanical frequencies can be optimized for damping and stiffness. It is expected that significant increases in the viscoelastic properties are found comparable to previous studies [1] but with the sensitive and impractical temperature control being replaced by an electric field of superior controllability.

Composite samples fabricated in section 3 are studied using the BES method to determine their effective viscoelastic properties under varying electromagnetic fields and/or at variable levels of temperature. Thereby, one can identify combinations of electrical (secondary tuning electromagnetic field) and mechanical (from primary driving electromagnetic field) frequencies that lead to significant changes in stiffness and damping. In addition, experimental campaigns can identify optimal fabrication techniques of composites (including, e.g., doping of ferroelectric ceramics, particle preparation, volume fraction selection).

In one or more embodiments, rectangular samples (ca. 5×1×20 mm) of the fabricated composite materials are polished and prepared for viscoelastic testing. Experiments use BES, as described in section 1 and FIG. 2 to characterize the dynamic moduli as well as the damping capacity (in terms of the loss tangent) of the composites at designated mechanical frequencies between 0.01-200 Hz (well below the first resonant frequency of the specimen to avoid any resonant phenomena, e.g. at least 25% less than the first resonant frequency) or up to 1 MHz (when including the full resonant spectrum).

Thus, one or more embodiments include discovery of a novel class of engineered materials with controllable mechanical properties, particularly (and for example) combining the rare find of high damping (effectively suppressing harmful vibrations) and high stiffness (minimizing deformations under applied loads). FIG. 6 confirms that PZT under appropriately controlled field (determined by the new apparatus) can lead to strong damping increases by more than 600% in stiff ceramics. Furthermore, combining a stiff ceramic matrix material with ferroelectric inclusions that undergo structural changes upon changing an applied tuning electromagnetic field promises the unique chance to design composite materials whose properties (especially, whose damping) can be enhanced dramatically by the push of a button.

5. Process Steps

Figure 7:
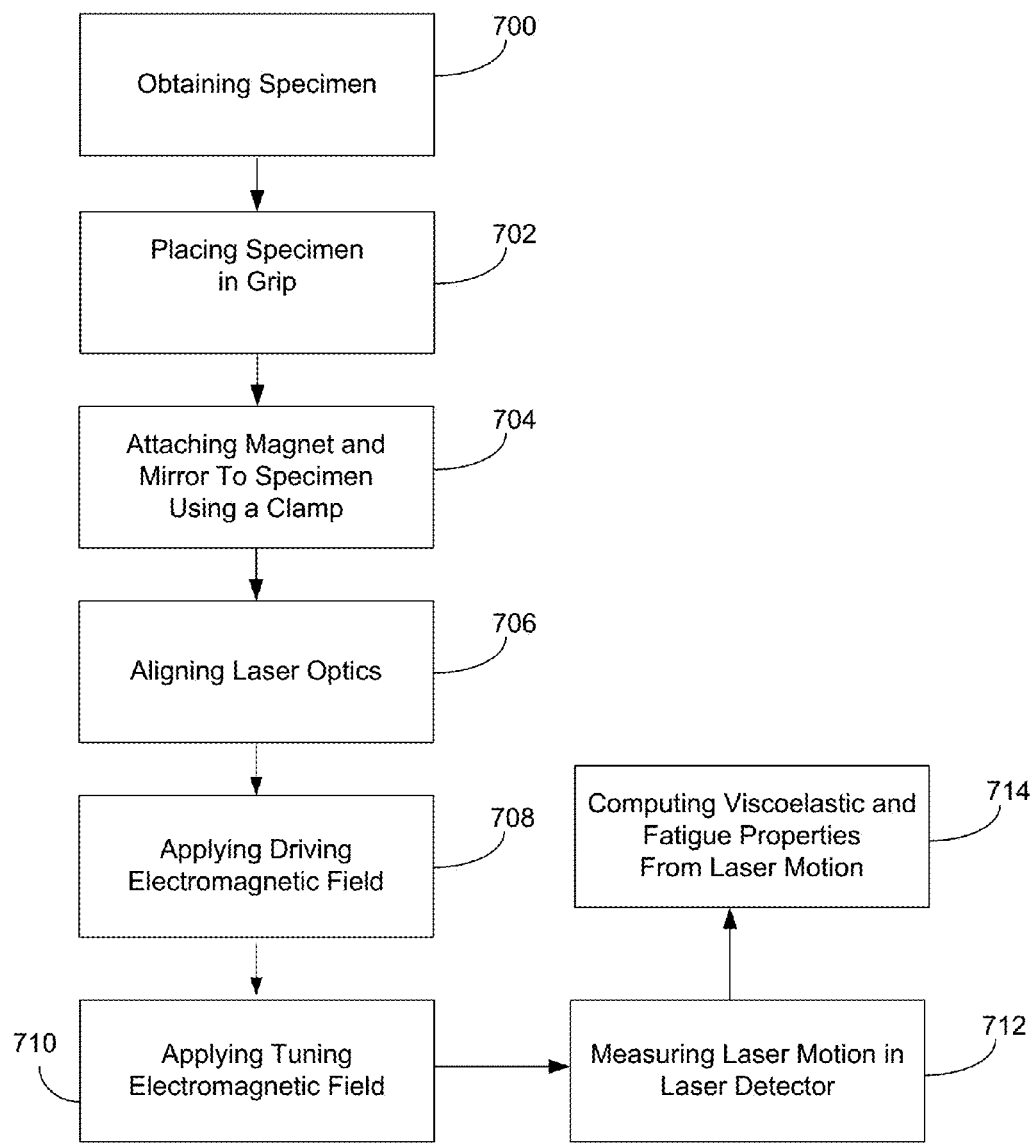
FIG. 7 is a flowchart illustrating the individual steps that are part of a method of testing the electro-thermo-mechanical properties of the material, according to one or more embodiments of the invention.

FIG. 7 illustrates a method for fabricating a material and a method and apparatus for testing a material/one or more components of the material, according to one or more embodiments. The method and apparatus measure one or more mechanical properties (e.g., viscoelastic properties and/or fatigue life) of the material during application of a secondary tuning electromagnetic field to the material that induces a structural or phase transition in the material.

Block 700 represents fabricating, providing, or obtaining the specimen to test in the apparatus. Specimens can be fabricated (e.g. using the method described in section 3) by methods of powder-metallurgy (including particle preparation and plating; powder blending, compacting, sintering; heat treatment; and sample preparation). The appropriate fabrication compositions can be determined by carrying out experiments with the apparatus to determine optimal compositions and microstructural designs leading to the desired material properties (e.g. high-stiffness and high-damping).

The following steps describe testing, e.g., using the BES set up described in section 1 (FIGS. 2(a)-(k)).

Block 702 represents placing (fixing, holding) the specimen comprising the material inside the apparatus using a grip (or a means to grip or for gripping the specimen), whereby the grip must be electrically isolated from the specimen and the secondary tuning electromagnetic field applied to the specimen. Upon tightening the grip, the conductive layer on the surface of the grips (e.g. copper tape) forms an electrical connection to the electrodes on the specimen. The conductive layer is then connected to a waveform generator via wire leads. Thus, the specimen grip electrically isolates the specimen from the apparatus and applies the secondary tuning electromagnetic fields. A vacuum chamber can enclose at least the material to enable measurement of the mechanical response under ambient pressures from atmospheric pressure (1000 mbar) down to $2*10^{-6}$ mbar. The chamber can have up-and-down-sliding capability to allow for installation of the specimen.

Block 704 represents attaching a clamp to the specimen (e.g. via set screws). The clamp contains a permanent magnet and mirror and attaches the magnet and mirror to the specimen. The clamp is electrically isolated from the specimen. The magnet applies a mechanical force to the specimen when placed inside the driving electromagnetic field and the mirror reflects an incoming ray of light from a laser into a detector. The mechanical response of the specimen is detected due to the reflected laser beam moving in the detector.

Block 706 represents the process of aligning laser optics (a laser beam) to reflect off of the mirror on the clamp attached to the specimen and go into a detector. The laser can be positioned to emit and focus a laser beam on the mirror attached to the specimen, and the detector can be positioned to receive the laser beam reflected from the mirror to detect a specimen motion. The distance between the specimen and the detector is chosen such that the response of the material causes a large enough motion in the detector that can be measured. For one embodiment of the invention, this distance is approximately two feet.

Block 708 represents turning on/generating and applying the primary driving electromagnetic field (e.g, using one or more electromagnetic coils). In one embodiment, the coils can allow for multiaxial testing of the specimen. In one embodiment of the invention the primary driving electromagnetic field is controlled by a waveform generator which allows for a particular amplitude and frequency of the driving voltage to the Helmholtz coils to be selected from a range of 0-10 V and 0.01-200 Hz (to avoid resonance phenomena), respectively. In one embodiment of the invention, the primary driving electromagnetic field produces strains in the specimen of $10^{-3}$ or less. The permanent magnet can convert the applied primary electromagnetic field to a mechanical force on the specimen and the mechanical force can cause the mechanical response of the material in the specimen.

Block 710 represents turning on and applying the secondary tuning electromagnetic field and/or varying the temperature of the material. The material's viscoelastic and/or fatigue life may be altered by application of the secondary tuning electromagnetic field and/or the selected temperature.

An electronic circuit can be used to apply one or more secondary tuning electromagnetic fields to the material, wherein a stiffness, damping, and fatigue life of the material in the specimen are altered by the secondary tuning electromagnetic fields. In one embodiment of the invention, the secondary tuning electromagnetic field is controlled by a waveform generator whose voltage is amplified by an amplifier. Typically, the waveform generator and amplifier capabilities are chosen to apply an electric field to the specimen of up to 5 MV/m and at various frequencies (e.g, 1 mHz to at least 10 Hz).

In one embodiment, radiant heater elements can be placed such that the specimen receives radiant energy from the heater elements and the radiant heater controls the selected temperature of the specimen up to 350° C. and without airflow.

In one or more embodiments, the secondary tuning electromagnetic field and/or temperature can induce a structural transition in the material.

Block 712 entails measuring the response of the specimen to the applied driving and tuning electromagnetic fields, which changes the position of the reflected laser beam in the detector (measuring laser motion in the detector that results from the mechanical response of the specimen).

Block 714 represents determining the material's physical properties (e.g., viscoelastic and/or fatigue). In one embodiment of the invention, the material's stiffness (e.g. Youngs modulus) and damping (e.g. loss tangent) is computed (e.g, in a computer) from a lock-in amplifier where the motion of the laser in the detector (corresponding to the specimen motion) is the input to the lock-in amplifier and the primary driving electromagnetic field waveform is the reference for the lock-in amplifier. Thus, the material's viscoelastic and/or fatigue properties can be measured by a mechanical response of the material caused or produced by applying the primary driving electromagnetic field during application of the secondary tuning electromagnetic field and/or selected temperature.

In another embodiment of the invention, the relaxation and creep response of specimens, the cyclic mechanical response, as well as the effects of temperature on the relaxation, creep, and cyclic mechanical response can be measured using the output from the laser detector. Further testing can be performed for various amplitudes and frequencies of the driving and tuning electromagnetic fields as well as under different temperature conditions when using the vacuum chamber. These data are recorded using an oscilloscope and/or a computer.

The data obtained by repeating Blocks 710-714 (which were previously unavailable) can be used to determine what materials and material microstructures (e.g. ferroelectrics and ferroelectric composites) lead to an optimal response of the material (e.g. certain viscoelastic properties such as high stiffness and high damping) to the secondary tuning electromagnetic field as well as the effects of temperature, which are important for using such novel materials in technological applications.

The data can also be used to select one or more of the electromagnetic fields and/or the temperature that obtain a certain viscoelastic and/or fatigue property. For example, FIG. 6 illustrates a ferroelectric material having one or more selected viscoelastic properties and/or a fatigue life that are altered/selected by application of a secondary tuning electromagnetic field to the ferroelectric material by an electronic circuit, wherein the viscoelastic properties and fatigue life are measured by a mechanical response of the material caused by application of a primary driving electromagnetic field to the material. FIG. 6 shows the secondary tuning electromagnetic field changes the material's stiffness by 50% or more and increases the material's damping by 500% or more, as compared to without application of the secondary tuning electromagnetic field.

6. Possible Modifications and Variations

The BES experimental setup can be further improved and developed based on the measurements and fabrication described in this specification. New materials fabrication techniques can also be developed based on the measurements and fabrication described in this specification.

The new BES is required for the high-accuracy viscoelastic measurements described in sections 3-5. However, the proposed device promises to serve numerous future applications by characterizing the mechanical and physical properties of solids, e.g., for studies of creep and relaxation of piezoelectric actuators and sensors, for fatigue life testing of ferroelectric materials for energy devices, and for elevated-temperature close-to-vacuum testing of aerospace technologies, including aircraft and helicopter components.

One or more embodiments of the invention deliver a proof of concept for the envisioned tunable performance, for the example of ferroelectric ceramics or of ceramic matrix-ferroelectric inclusion composites. While the ceramic matrix phase (chosen here to simplify the application of electric fields) might be well suited for applications in civil engineering, it is less appropriate for light-weight aircraft design or machine components. However, one or more embodiments of the concepts described herein can be extensively transformed to a variety of materials of scientific and industrial interest. Therefore, one or more embodiments of the invention can lay the foundation for new tunable materials of enormous commercial potential. For example, one or more embodiments of the invention can provide a new class of composite materials with electrically controllable properties for advanced shock absorption and vibration attenuation.

7. Advantages, Improvements, Significance, and Vision Apparatus

One or more embodiments of the invention provide a BES apparatus for testing piezoceramic materials. These one-of-a-kind experimental apparatuses can investigate the electrically tunable viscoelastic properties of materials (e.g., of composite materials) containing electro-active constituents, to determine how the viscoelastic moduli of stiff composite materials can be determined accurately over wide ranges of mechanical frequencies, and to identify specifications of the applied bias electric field to induce maximal changes of the material properties.

The fundamental concept of BVS provides the basis for the experimental apparatus according to one or more embodiments. Unfortunately, the well-known [3] (but not commercially available) set-up of BVS test devices does not allow for full electro-thermo-mechanical characterization of envisioned ferroelectric and ferroelectric composite materials for several reasons. Most importantly, the new device(s) according to one or more embodiments of the present invention include the application of two electromagnetic fields that are controlled independently and reduce interference to a minimum: one controllable field (called the secondary tuning electromagnetic field) induces a phase transformation in the ferroelectric material and ferroelectric composite phases dramatically altering its physical properties (e.g. viscoelastic and fatigue properties), another electromagnetic field (called the primary driving electromagnetic field) applies a force to the permanent magnet attached to the specimen allowing for its viscoelastic and fatigue properties to be measured.

However, the required electric field within the specimen to tune the domains necessitates the application of electrodes to the specimen. In current realizations of BVS, metallic grips and clamps (containing the magnet and mirror) would short circuit such surface electrodes preventing an electric field from forming within the material and inducing a phase transition. In addition current realization of BVS utilize airflow over the specimen for temperature control, which causes unwanted vibrations in the specimen during testing that affects measurements of its viscoelastic and fatigue properties. The new experimental apparatus(es) according to one or more embodiments of the invention overcome those deficiencies and allow for high-precision measurements of the viscoelastic properties while controlling the electric field within the specimen. Specifically, electrode layers of marginal thickness are applied directly onto the specimen (e.g., by sputtering), and the electric field is applied through a specialized electrically isolated specimen gripping system. An electrically isolated and non magnetic clamp for attaching the permanent magnet and mirror to the specimen was also designed.

The experimental apparatuses according to one or more embodiments are an enormous asset because they allow for the experimental verification of novel materials with tunable properties and the characterization of electro-thermo-mechanically-coupled properties of existing materials, which can only otherwise be pursued theoretically and computationally. Moreover, one or more embodiments of the novel materials disclosed in present invention require the design of the new, one-of-a-kind experimental apparatus(es) that have been planned, custom-built and tested by the inventors. In addition, the novel experimental system can also have general utility for future applications at the intersection of electromagnetic and mechanical properties of solids.

Materials

The successful suppression of mechanical vibration is a crucial challenge across innumerable fields of science and technology. The vibration of structural components caused by external or internal excitations occurs over numerous length and time scales and, most importantly, often leads to catastrophic failure. Examples comprise the shaking of buildings from natural causes such as tectonic motion or extreme weather events, the excitation of machine components due to rotating machine parts, or the vibration in air- or spacecraft due to turbulence or propulsion.

Besides, vibration is harmful to the human physiology. For all those reasons, we need capabilities to suppress mechanical vibrations, and such capabilities exist, including active damping (where sensors and actuators control the system's structure to cancel vibration), passive damping (where the system is designed to attenuate specific frequencies), and combinations thereof. As a common feature, all those solutions suffer from one of two major deficiencies.

First, they require significant modifications to the system's structure which is prohibitive for many technological applications such as in light-weight air- and spacecraft design.

Second, those few methods that indeed generate new materials with high damping usually fall short of other mechanical properties (e.g., strength or stiffness) and, in particular, they are not tunable; i.e. the damping characteristics are unchangeable after fabrication and installation.

One or more embodiments of the present invention provide a method of discovering an entirely new class of materials which offer tunable high-damping capabilities combined with high stiffness. This novel and transformative paradigm of material design (e.g., extreme composites) rests upon the counter-intuitive mechanical response of phase transforming materials when constrained in their deformation behavior. The counter-intuitive and recently developed concept of utilizing constrained small-scale instabilities (here, domain wall motion and polarization changes) can give rise to unprecedented damping and stiffness increases.

One or more embodiments of the invention provide a clear overview of viable inclusion materials for proposed composites. Composite materials with ferroelectric inclusions can be fabricated and characterized to identify composite systems with high stiffness and high damping controllable by applying electric fields, as outlined in sections 3 and 4. For example, our newly-developed experimental BES apparatus has been fabricated and used to characterize the electro-mechanical behavior of lead-zirconate-titanate (PZT), see FIG. 6. Experiments performed under various combinations of mechanical and electrical loading rates revealed their impact on the effective stiffness and damping of the material (variable-temperature experiments are underway). Finally, powder-metallurgical material processing methods and analysis techniques have been explored to develop novel composites by embedding ferroelectric inclusions in a stiff matrix.

Potential applications for the new apparatus(es) of one or more embodiments of the present invention include, e.g., viscoelastic testing and/or mechanical fatigue testing over wide ranges of temperature and ambient pressure, electrical fatigue testing over wide ranges of temperature and ambient pressure, or combined electrical and mechanical testing over wide ranges of temperature and ambient pressure. The generated and presently-unavailable data can be used to inform computational models for engineering design and to understand the underlying physical material behavior. The new materials of one or more embodiments of the present invention promise beneficial viscoelastic properties for applications ranging from seismic safety, to vibration attenuation in air- and spacecraft, to physiological vibration insulation.

References

The following references are incorporated by reference herein.

[1] T. M. Jaglinski, D. M. Kochmann, D. S. Stone, and R. S. Lakes, Science 315 (2007), 620-622.

[2] D. M. Kochmann, Thesis, University of Wisconsin-Madison, 2006.

[3] R. S. Lakes, Rev. Sci. Instruments 75 (2004), 797-810.

[4] R. S. Lakes, Viscoelastic Solids, CRC Press (1999).

[5] C. B. Sawyer, C. H. Tower, Phys. Rev. 35 (1929), 269-273.

[6] P. Yang, R. H. Morre, and G. R. Burns, J. Appl. Phys. 91 (2002), no. 10028.

[7] I. Franke et al., J. Phys. D: Appl. Phys. 38 (2005), 749-753.

[8] Y. Avrahami, H. L. Tuller, J. Electroceram. 13 (2004), 463-469.

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An apparatus, comprising:
an electronic circuit for applying one or more secondary tuning electromagnetic fields to a specimen comprising a material, wherein one or more properties of the material are altered by the one or more secondary tuning electromagnetic fields;
one or more electromagnetic coils for generating one or more primary driving electromagnetic fields that produce one or more mechanical responses of the specimen comprised of the material during application of the one or more secondary tuning electromagnetic fields, or a selected temperature, or the selected temperature and the one or more secondary tuning electromagnetic fields;
a specimen grip for physically holding the specimen inside the apparatus, wherein the specimen grip electrically isolates the specimen from the apparatus while applying the one or more secondary tuning electromagnetic fields;
a clamp for attaching a permanent magnet to the specimen, wherein;
the permanent magnet converts the applied one or more primary driving electromagnetic fields to one or more mechanical forces on the specimen,
the one or more mechanical forces cause the one or more mechanical responses of the material in the specimen, and
the clamp is electrically isolated from the specimen;
a detector positioned to receive a laser beam reflected from a mirror attached to the specimen to detect one or more specimen motions,
a laser positioned to focus the laser beam on the mirror; and
a vacuum chamber enclosing at least the material to enable measurement of the one or more mechanical responses under ambient pressures from atmospheric pressure (1000 mbar) down to a vacuum pressure; and
wherein the one or more specimen motions result from the one or more mechanical responses and are used to measure the one or more properties of the material during application of the one or more secondary tuning electromagnetic fields, or the selected temperature, or the one or more secondary tuning electromagnetic fields and the selected temperature.

2. The apparatus of claim 1, wherein the vacuum chamber enables measurement of the one or more mechanical responses under ambient pressures from atmospheric pressure (1000 mbar) down to $2*10^{-6}$ mbar.

3. The apparatus of claim 2, wherein the vacuum chamber is opened and closed via vertical rails allowing for up-and-down-sliding for installation of the specimen.

4. The apparatus of claim 2, further comprising radiant heater elements placed inside the vacuum chamber such that the specimen placed inside the vacuum chamber receives radiant energy from the radiant heater elements and the radiant heater elements control the selected temperature of the specimen up to 350° C. and without airflow.

5. The apparatus of claim 4, wherein the selected temperature induces a structural transition in the material that alters one or more of the properties.

6. The apparatus of claim 1, further comprising a plurality of the coils of different spatial orientations to induce the one or more (simultaneous) primary driving electromagnetic fields that allow for multiaxial mechanical testing of the specimen.

7. The apparatus of claim 1, wherein the one or more secondary tuning electromagnetic fields induce a structural transition in the material that alters one or more of the properties.

8. The apparatus of claim 1, wherein the material comprises a ferroelectric material.

9. The apparatus of claim 1, wherein the material comprises a ferroelectric material having the one or more properties that are tuned by application of the one or more secondary tuning electromagnetic fields, or the selected temperature, or the one or more secondary tuning electromagnetic fields and the selected temperature.

10. The apparatus of claim 1, for performing Broadband Electromechanical Spectroscopy of the specimen, further comprising;
a waveform generator for passing current through the one or more electromagnetic coils such that one or more electromechanical responses of the specimen are measured as a function of one or more mechanical frequencies in a range of 0.01 Hz to 1 MHz and as a function of the one or more primary driving electromagnetic fields comprising one or more electric fields, wherein the one or more electric fields applied to the specimen can be one or more wave-forms having a frequency in a range of 1 mHz to at least 10 Hz.

11. The apparatus of claim 1, wherein the electromagnetic fields are selected to measure the one or more viscoelastic properties chosen from dynamic Young modulus, shear modulus, damping capacity, creep response, relaxation response, mechanical long-term stability including fatigue, one or more electromechanically-coupled properties, and electrical fatigue.

12. The apparatus of claim 1, wherein the electromagnetic fields are selected to measure the one or more properties of the material including one or more electromechanically-coupled properties, or an electrical fatigue property, or the one or more electromechanically-coupled properties and the electrical fatigue property.

13. The apparatus of claim 1, wherein a structure of the material is such that the one or more secondary tuning electromagnetic fields change the materials's stiffness by 50% or more and increase the material's damping by 500% or more, as compared to without application of the one or more secondary tuning electromagnetic fields.

14. The apparatus of claim 1, wherein the one or more properties include one or more viscoelastic properties.

15. the apparatus of claim 1, wherein the one or more properties include a stiffness.

16. The apparatus of claim 1, wherein the one or more properties include a damping.

17. The apparatus of claim 1, wherein the one or more properties include a fatigue life.

18. A method for testing a material, comprising:
using an electronic circuit to apply one or more secondary tuning electromagnetic fields to a specimen comprising a material, wherein:
the one or more secondary tuning electromagnetic fields, or a selected temperature, or a selected temperature and the one or more secondary tuning electromagnetic fields, alter one or more properties of the material including one or more viscoelastic properties, or fatigue life, or the fatigue life and the one or more viscoelastic properties, and
the one or more properties are measured when the electronic circuit applies the one or more secondary tuning electromagnetic fields comprising one or more electric fields having a magnitude of up to 5 MV/m, and
a detector measures one or more motions of the specimen corresponding to one or more strain, induced in the specimen by one or more primary driving electromagnetic fields, of $10^{-3}$ or less.

19. the method of claim 18, further comprising:
performing Broadband electromechanical Spectroscopy of the specimen, comprising measuring one or more electromechanical responses of the specimen as a function of one or more mechanical frequencies in a range of 0.01 Hz to 1 MHz and as a function of the one or more electric fields, wherein the one or more electric applied to the specimen can be one or more wave-forms having a frequency in a range of 1 mHz to at least 10 Hz.

20. A method for testing a material, comprising:
using one or more electronic circuits to apply one or more secondary electromagnetic fields, or a selected temperature, or the one or more secondary electromagnetic fields and a selected temperature, to a material to change one or more properties of the material, the one or more properties including a viscoelastic property, or a fatigue property, or the viscoelastic property and the fatigue property;
measuring the one or more properties of the material during application of the one or more secondary electromagnetic fields, or the selected temperature, or the one or more secondary electromagnetic fields and the selected temperature, wherein the one or more properties are measured from one or more mechanical responses of the material produced by one or more primary driving electromagnetic fields applied to the material during application of the one or more secondary tuning electromagnetic fields, or the selected temperature, or the one or more secondary electromagnetic fields and the selected temperature; and
selecting one or more of the secondary electromagnetic fields, or the temperature, or the one or more secondary electromagnetic fields and the temperature, that obtain the one or more properties including a certain viscoelastic property, or a certain fatigue property, or the certain viscoelastic property and the certain fatigue property.

21. The method of claim 20, further comprising:
gripping a specimen comprising the material inside an apparatus;
generating the one or more primary driving electromagnetic fields, from one or more electromagnetic coils, that produce the one or more mechanical responses of the specimen during application of the one or more secondary electromagnetic fields to the material, wherein the coils produce the one or more mechanical responses of the specimen when a permanent magnet is attached to the specimen;
emitting a laser beam from a laser to the specimen; and
detecting one or more motions of the laser beam reflected from the specimen in a detector, wherein the one or more motions result from the one or more mechanical responses and are used to measure the one or more properties of the material during application of the one or more secondary electromagnetic fields, or the selected temperature, or the one or more secondary electromagnetic fields and the selected temperature.

22. A composition of matter, comprising:
a ferroelectric material having a stiffness and a damping that are altered by application of a tuning electromagnetic field to the ferroelectric material by an electronic circuit, wherein the ferroelectric material's structure is such that;
the stiffness is changeable by 50% or more by application of the tuning electromagnetic field as compared to without application of the tuning electromagnetic field, and
the damping is increasable by 500% or more by application of the tuning electromagnetic field as compared to without application of the tuning electromagnetic field.

\* \* \* \* \*